United States Patent

Beekhuis et al.

[11] 3,960,924
[45] June 1, 1976

[54] PROCESS FOR THE PREPARATION OF UNSATURATED CYANOCARBONYL COMPOUNDS

[75] Inventors: Gerrit E. Beekhuis, Geleen; Leonardus H. Geurts, Sittard, both of Netherlands

[73] Assignee: Stamicarbon B.V., Geleen, Netherlands

[22] Filed: Mar. 11, 1975

[21] Appl. No.: 557,380

[30] Foreign Application Priority Data
Mar. 11, 1974 Netherlands.................. 7403200

[52] U.S. Cl............................ 260/465.9; 260/464
[51] Int. Cl.² ........................................ C07C 120/00
[58] Field of Search.................... 260/464, 465.9

[56] References Cited
UNITED STATES PATENTS

| | | | |
|---|---|---|---|
| 2,409,086 | 10/1946 | Walker.................. | 260/465.8 R |
| 2,850,519 | 9/1958 | Krimm.................. | 260/464 |
| 3,529,009 | 9/1970 | aus der Funten.......... | 260/465.9 X |

*Primary Examiner*—Joseph P. Brust
*Attorney, Agent, or Firm*—Cushman, Darby & Cushman

[57] ABSTRACT

The compounds

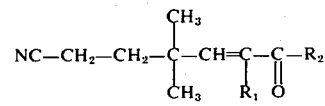

wherein each of $R_1$ and $R_2$ is H or alkyl of 1 to 5 carbon atoms, a cycloalkyl group of 5 to 10 carbon atoms or $R_1$ and $R_2$ bonded together through two adjacent carbon atoms form a saturated cycloaliphatic ring of 5 to 12 carbon atoms, are prepared by step (1) reacting acrylonitrile with isobutyraldehyde in the liquid phase to form 2,2-dimethyl-4-cyanobutyraldehyde and step (2) by reacting 2,2-dimethyl-4-cyanobutyraldehyde with a carbonyl compound of the general formula

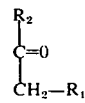

wherein $R_1$ and $R_2$ are as defined above, wherein step (a) and step (b) are undertaken in the presence of a catalyst which is piperidine or a primary amine and/or a Schiff base and in the presence of an acid compound.

7 Claims, No Drawings

PROCESS FOR THE PREPARATION OF UNSATURATED CYANOCARBONYL COMPOUNDS

The invention relates to a process for the preparation of unsaturated cyanocarbonyl compounds and to the compounds produced thereby.

BACKGROUND OF THE INVENTION

U.S. Pat. No. 3,529,009 is related to a process wherein an aldehyde or ketone will undergo a condensation reaction with 2,2-dimethyl-4-cyanobutyraldehyde in the presence of a basic catalyst. In the case of acetone, in the presence of solid potassium hydroxide as a catalyst the compound 5,5-dimethyl-7-cyanoheptene-3-one-2 can be obtained in a yield of 61.1%. According to U.S. Pat. No. 2,409,086, the 2,2-dimethyl-4-cyanobutyraldehyde required for this reaction can be prepared from isobutyraldehyde and acrylonitrile by means of an alkaline catalyst with a yield of 35–40% of the theoretical yield.

Thus, the prior art processes for reacting isobutyraldehyde, acrylonitrile, and acetone to form unsaturated cyanocarbonyl compounds are impractical because of the inefficiency of the processes and the resulting cost.

The discovery of the invention is in the use of catalysts which can give a much higher yield in the preparation of such unsaturated cyanocarbonyl compounds. Thus, the invention is an improvement in the prior art processes for preparing unsaturated cyanocarbonyl compounds.

SUMMARY OF THE INVENTION

The invention provides a process for the preparation of cyanocarbonyl compounds of the general formula $$NC-CH_2-CH_2-\underset{\underset{CH_3}{|}}{\overset{\overset{CH_3}{|}}{C}}-CH=\underset{\underset{R_1}{|}}{C}-\underset{\underset{O}{\|}}{C}-R_2$$

where, each of $R_1$ and $R_2$ is hydrogen, an alkyl group of 1 to 5 carbon atoms, a cycloalkyl group of 5 to 10 carbon atoms or $R_1$ and $R_2$ bonded together through two adjacent carbon atoms, form a saturated ring structure of 5 to 12 carbon atoms, which process is characterized by (1) reacting acrylonitrile in the liquid phase with isobutyraldehyde, to form a resulting reaction product and then reacting said reaction product likewise in the liquid phase, with a carbonyl compound of the general formula $$\underset{\underset{CH_2-R_1}{|}}{\overset{\overset{R_2}{|}}{C}}=O$$

where $R_1$ and $R_2$ have the definitions set forth above, wherein both reactions are carried out in the presence of piperidine or a primary amine and/or a Schiff base, as a catalyst, and in the presence of an acid compound.

In addition to the above advantage of a higher yield, the process according to the invention has the advantage that no solid catalyst is required and can thus be carried out in a homogeneous liquid phase.

DETAILED DESCRIPTION OF THE INVENTION

The compounds $$NC-CH_2-CH_2-\underset{\underset{CH_3}{|}}{\overset{\overset{CH_3}{|}}{C}}-CH=\underset{\underset{R_1}{|}}{C}-\underset{\underset{O}{\|}}{C}-R_2$$

wherein each of $R_1$ and $R_2$ is H or alkyl of 1 to 5 carbon atoms, a cycloalkyl group of 5 to 10 carbon atoms or $R_1$ and $R_2$ bonded together through two adjacent carbon atoms form a saturated cycloaliphatic ring of 5 to 12 carbon atoms, are prepared by step (1) reacting acrylonitrile with isobutyraldehyde in the liquid phase to form 2,2-dimethyl-4-cyanobutyraldehyde and step (2) by reacting 2,2-dimethyl-4-cyanobutyraldehyde with a carbonyl compound of the general formula $$\underset{\underset{CH_2-R_1}{|}}{\overset{\overset{R_2}{|}}{C}}=O$$

wherein $R_1$ and $R_2$ are as defined above, wherein step (a) and step (b) are undertaken in the presence of a catalyst which is piperidine or a primary amine, a Schiff base or mixtures thereof and in the presence of an acid compound.

Carbonyl compounds of the general formula $$\underset{\underset{CH_2-R_1}{|}}{\overset{\overset{R_2}{|}}{C}}=O$$

wherein $R_1$ and $R_2$ are as defined above, include aliphatic aldehydes such as acetaldehyde, propionaldehyde, butyraldehyde, and the like; ketones such as acetone, methyl ethyl ketone, methyl isopropyl ketone, methyl isobutyl ketone, and the like; and cycloaliphatic ketones such as cyclopentanone, cyclohexanone, α- and β-tetralones, and the like.

The catalyst may be piperidine, a primary amine, a Schiff base or mixtures thereof.

As is known in the art said Schiff base is formed by reacting the primary amine with an aldehyde or ketone. Aldehydes and ketones which may be used to form the Schiff base are of the formula $$R_A-\underset{\underset{}{\overset{\overset{O}{\|}}{C}}}{}-R_B$$

wherein $R_A$ is H, alkyl or aryl of 1 to 6 carbon atoms and $R_B$ is alkyl or aryl of 1 to 6 carbon atoms; examples of said aldehydes and ketones include propionaldehyde, n- and isobutyraldehyde, acetone, methyl isobutyl ketone, cyclohexanone and the like.

The terms primary amine and Schiff base, as used here, also include compounds that contain another functional group, beside the primary amino group or the N-substituted imine group, e.g., an amino acid.

Some examples of catalysts that may be used in the reaction according to the invention are methyl amine, ethyl amine, n-propyl amine, isopropyl amine, n-butyl amine, isobutyl amine, secondary-butyl amine, secondary-pentyl amine, n-hexyl amine, cyclopentyl amine, cyclohexyl amine, hexamethylene diamine, ε - amino caproic acid, piperidine, and the Schiff bases of a ketone or aldehyde with one of the aforementioned primary amines.

Particularly suitable catalysts are isopropyl amine, cyclohexyl amine, and the Schiff bases derived from these amines and piperidine. The amount of catalyst may be varied. For practical purposes, an amount of 0.01 to 0.25 mole of catayst per mole of isobutyraldehyde to be converted is sufficient.

The acid compound may be an organic or an inorganic compound which contains an acidic proton. The organic acids may be aliphatic or aryl compounds which contain an acidic proton, wherever said alkyl or aryl contain 1 to 6 carbon atoms. The organic compounds which contain an acidic proton and can be used in accordance with the process of the invention include acetic acid, adipic acid, benzoic acid, phenol, and caproic acid. Inorganic acid compounds which may be used include hydrochloric acid, phosphoric acid, sulfuric acid and ammonium chloride.

In principle, any compound that can reduce the pH of a neutral aqueous solution and/or contains a functional acid group is suitable as the acid compound. Only a small amount of acid compound, e.g., 0.01–0.5 mole per mole of catalyst, is required for step (a) and step (b) of the reaction according to the invention. If the catalyst also contains an acid group, such as, for instance, in the case of $\epsilon$-aminocaproic acid, the addition of another acid compound may be omitted.

In the process according to the invention, the reaction between the acrylonitrile and the aldehyde is preferably carried out with about equimolar amounts, and, in the subsequent reaction of the resulting addition product with the carbonyl compound, preferably an excess amount of carbonyl compound, is used, e.g., 2–5 moles per mole of addition product.

Both reactions in the process according to the invention are preferably carried out at temperatures ranging from 75° to 250°C. For, at a temperature over 250° C, the yield is unfavorably affected, while the reactions proceed slowly at a temperature below 75° C. The pressure may be varied and is not critical. Naturally, the pressure should be so chosen in combination with the temperature that the reaction can be carried out in the liquid phase, whether or not in the presence of a solvent or diluent. The reactions according to the invention may be carried out in the presence of any inert solvent or diluent, but the use of such an agent is not required.

In the process according to the invention, the resulting addition product of the first reaction step of the process may be separated from the reaction mixture, e.g., by distillation, after the first reaction, and then can be subjected to the second reaction. It is also possible after the first reaction to add the carbonyl compound for the second reaction to the resulting reaction mixture, after addition of an additional amount of catalyst and/or acid compound to the reaction mixture. Several realizations are possible.

The invention will be further elucidated in the following examples.

EXAMPLE 1

A stainless-steel autoclave with a capacity of 5 liters is fed with 1080 grams of isobutyraldehyde (15 moles), 795 grams of acrylonitrile (15 moles), 74 grams of cyclohexyl amine (0.75 mole), and 18 grams of benzoic acid (0.15 mole). The mixture is heated to 140° C with stirring and then gradually heated further for 4 hours until a temperature of 170° C is finally reached. The autoclave is cooled to room temperature and the reaction mixture is separated by distillation into the following fractions:

Fraction 1: Boiling range 60°–95° C at atmospheric pressure, weight 203.4 grams.

Fraction 2: Boiling range 101°–115° C at 10 mm Hg, weight 129.6 grams. Fraction 3: Boiling range 115°–117° C at 10 mm Hg, weight 1263.0 grams.

Fraction 1 contains 85.5 grams of isobutyraldehyde and 111.0 grams of acrylonitrile according to gas-chromatographic analysis.

Fraction 2 contains 103.7 grams of 2,2-dimethyl-4-cyanobutyraldehyde and fraction 3 contains 1251.5 grams of this compound according to gas-chromatographic analysis. Consequently the yield of 2,2-dimethyl-4-cyanobutyraldehyde is 84.0% relative to the amount of acrylonitrile converted and 78.5% relative to the amount of isobutyraldehyde converted.

The 2,2-dimethyl-4-cyanobutyraldehyde is then coupled with acetone to form, 5,5-dimethyl-7-cyanoheptene-3-one-2. To this end 630.7 grams of fraction 3 (which contains 5 moles of dimethyl cyanobutyraldehyde), 1450 grams of acetone (25 moles), 24 grams of cyclohexyl amine (0.25 mole), and 6 grams of benzoic acid (0.05 mole) are fed to a stainless-steel autoclave with a capacity of 5 liters, and this mixture is then heated to 190° C. After a reaction period of 9 hours, the autoclave is cooled and the reaction mixture is distilled. The excess acetone and the water formed are removed at atmospheric pressure. Next, the following fractions are collected at reduced pressure:

Fraction 4: Boiling range 55°–110° C at 0.2 mm Hg, weight 221.2 grams.

Fraction 5: Boiling range 110°–113° C at 0.2 mm Hg, weight 418.3 grams.

According to gas-chromatographic analysis, fraction 4 contains 172.9 grams of dimethyl cyanobutyraldehyde and 23.6 grams of dimethyl cyanoheptenone, and fraction 5 contains 25.2 grams of dimethyl cyanobutyraldehyde and 391 grams of dimethyl cyanoheptenone.

The yield of 5,5-dimethyl-7-cyanoheptene-3-one-2 is consequently 73.6% calculated to the 2,2-dimethyl-4-cyanobutyraldehyde converted. 5,5-dimethyl-7-cyanoheptene-3-one-2 can be obtained in a pure state by redistillation of fraction 5.

EXAMPLE II

An autoclave with a capacity of 1 liter is fed with 216 grams of isobutyraldehyde (3 moles), 159 grams of acrylonitrile (3 moles), 12.8 grams of piperidine (0.15 mole), and 1.8 grams of acetic acid (0.03 mole), and this mixture is heated at 170° C for 3 hours. After cooling the reaction mixture is analyzed by means of gas-chromatography.

The mixture contains 4.3% by weight of isobutyraldehyde, 10.3% by weight of acrylonitrile, and 66.7% by weight of 2,2-dimethyl-4-cyanobutyraldehyde. Consequently, the yield of dimethyl cyanobutyraldehyde is 92.7% relative to the amount of acrylonitrile converted and 75.1% relative to the amount of isobutyraldehyde converted.

The volatile components, mainly acrylonitrile and isobutyraldehyde, are removed by heating the mixture to 70° C at a pressure of 100 mm Hg.

The residual mixture with a weight of 338.0 grams is then heated to 185° C in a 2-liter autoclave for 6 hours together with 580 grams of acetone (10 moles). The mixture is cooled. According to gas-chromatographic analysis the mixture contains 9.3% by weight of 2,2-dimethyl-4-cyanobutyraldehyde and 18.9% by weight of 5,5-dimethyl-7-cyanoheptene-3-one-2. The yield is consequently 75.3% calculated to the dimethyl cyanobutyraldehyde converted.

The compounds produced in accordance with the invention are useful in the preparation of diamines and as stabilizers, e.g., for nitric ester.

What is claimed is:

1. A process for the preparation of unsaturated cyanocarbonyl compounds of the general formula

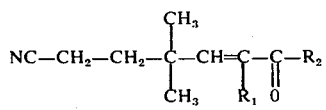

where, independently of each other, $R_1$ and $R_2$ represent hydrogen, an alkyl group with 1 to 5 carbon atoms, a cycloalkyl group with 5 to 10 carbon atoms, or, together with two adjacent carbon atoms, a saturated ring structure of 5 to 12 carbon atoms, comprising step (a) reacting acrylonitrile with isobutyraldehyde in the liquid phase to form 2,2-dimethyl-4-cyanobutyraldehyde and step (b) reacting 2,2-dimethyl-4-cyanobutyraldehyde with a compound of the formula

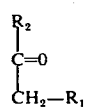

wherein, $R_1$ and $R_2$ are as defined above, wherein step (a) and step (b) are carried out in the presence of a catalyst which is piperidine, a primary amine, a Schiff base or mixtures thereof, and in the presence of an acid or an acidic compound, wherein each of step (a) and step (b) is carried out at a temperature of from 75° to 250°C. and wherein 0.01–0.25 mole of catalyst per mole of aldehyde to be converted is used in each of step (a) and step (b).

2. The process according to claim 1, characterized in that the catalyst used is isopropyl amine, cyclohexyl amine, a Schiff base of isopropyl amine, a Schiff base of cyclohexyl amine, or piperidine.

3. In the process according to claim 2, wherein $R_2$ is methyl and $R_1$ is hydrogen.

4. The process according to claim 1, wherein said acid or acid compound is an organic or an inorganic compound which contains an acidic proton.

5. The process according to claim 4, wherein said organic compound is an alphatic compound or aryl compound of 1 to 6 carbon atoms.

6. The process according to claim 4, wherein said acid is hydrochloric acid, phosphoric acid, sulphuric acid or ammonium chloride.

7. In a process for preparing compounds of the formula

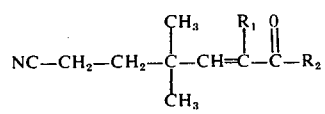

wherein each of $R_1$ and $R_2$ is H or alkyl of 1 to 5 carbon atoms, a cycloalkyl group of 5 to 10 carbon atoms or $R_1$ and $R_2$ bonded together through two adjacent carbon atoms form a saturated cycloalkyl ring of 5 to 10 carbon atoms, by reacting 2,2-dimethyl-4-cyanobutyraldehyde with a carbonyl compound of the formula

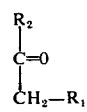

wherein $R_1$ and $R_2$ are as defined above, the improvement comprising a. preparing said 2,2-dimethyl-4-cyanobutyraldehyde by reacting acrylonitrile with isobutyraldehyde in the liquid phase; and b. then reacting 2,2-dimethyl-4-cyanobutyraldehyde with said carbonyl compound, wherein step (a) and step (b) are carried out in the presence of a catalyst which is piperidine, a primary amine, a Schiff base or mixtures thereof, and in the presence of an acid or an acidic compound wherein each of step (a) and step (b) is carried out at a temperature of from 75° to 250°C. and wherein 0.01–0.25 mole of catalyst per mole of aldehyde is used in each of step (a) and step (b).

* * * * *